United States Patent [19]

Fisher et al.

[11] 4,083,984

[45] Apr. 11, 1978

[54] 1-SUBSTITUTED PHENYL-4(1H)-PYRIDINONE HYDRAZONES AND COMPOSITION THEREWITH FOR TREATMENT OF COCCIDIOSIS

[75] Inventors: Michael H. Fisher, Bridgewater; William V. Ruyle, Scotch Plains, both of N.J.

[73] Assignee: Merck & Co., Inc., Rahway, N.J.

[21] Appl. No.: 813,930

[22] Filed: Jul. 8, 1977

Related U.S. Application Data

[62] Division of Ser. No. 743,388, Nov. 19, 1976.

[51] Int. Cl.$^2$ .................. A01N 9/22; C07D 211/18
[52] U.S. Cl. .................................... 424/263; 542/417
[58] Field of Search ................ 542/417; 424/226, 263

[56] References Cited

U.S. PATENT DOCUMENTS 3,829,492  8/1974  Miller et al. .................. 542/417 X
3,850,915  11/1974  Bruce ............................. 542/417

OTHER PUBLICATIONS

Hunig et al. "Azofarbstoffe Durch Oxydative Kupplung", in Annalen Der Chemie pp. 181, 182, 190, 191.

*Primary Examiner*—Allen B. Curtis
*Attorney, Agent, or Firm*—Walter Patton

[57] ABSTRACT

Novel 1-substitutedphenyl-4(1H)-pyridinone hydrazones are prepared by reacting 1-substitutedphenyl-4(1H)-pyridinone hydrazone with substituted benzaldehydes. The novel hydrazones are useful as anticoccidial agents.

15 Claims, No Drawings

1-SUBSTITUTED PHENYL-4(1H)-PYRIDINONE HYDRAZONES AND COMPOSITION THEREWITH FOR TREATMENT OF COCCIDIOSIS

This is a division of application Ser. No. 743,388 filed Nov. 19, 1976.

DISCLOSURE OF THE INVENTION

This invention relates to new and useful 1-substituted-phenyl-4(1H)-pyridinone hydrazones, as well as to the process for their preparation. In addition, this invention relates particularly to the prevention and treatment of coccidiosis in poultry. More particularly, this invention is concerned with the effectiveness of variously 1-substituted phenol-4(1H)-pyridinone hydrazones and with compositions containing these compounds for use in the prevention and treatment of coccidiosis.

Coccidiosis is a common and widespread poultry disease caused by a number of species of protozoan parasites of the genus Eimeria, including $E.$ $tenalla$, $E.$ $necatrix$, $E.$ $acervulina$, $E.$ $maxima$, $E.$ $hagani$, and $E.$ $brunetti$. $E.$ $tenella$ is the causative agent of a severe and often fetal infection of the caeca of chickens, which is manifested by severe and extensive hemorrhage, accumulation of blood in the caeca, and the passage of blood in the droppings. $E.$ $necatrix$ attacks the small intestine of the chick causing what is known as intestinal coccidiosis. Related species of coccidia such as $E.$ $meleagridis$ and $E.$ $adenoides$ are causative organisms of coccidiosis in turkeys. When left untreated, the severe forms of coccidiosis lead to poor weight gain, reduced feed efficiency and high mortality in fowl. The elimination or control of this disease is important in order to insure protecting a valuable source of food protein.

Therefore, one object of this invention is to provide new compounds which possess anticoccidial activity. Another object of this invention is to provide anticoccidial compounds active against $E.$ $tenella$, $E.$ $acervulina$, $E.$ $brunetti$, $E.$ $necatrix$ and E. maxima. Still another object is to provide a process for the preparation of said compounds. A further object of this invention is to provide novel compositions containing these 1-substitutedphenyl-4(1H)-pyridinone hydrazones as an active ingredient. Additional objects will become apparent upon further reading of this description.

According to this invention, it has been found that 1-substitutedphenyl-4(1H)-pyridinone hydrazones of formula (I) below and the corresponding non-toxic, pharmacologically acceptable salts are effective in the prevention and treatment of coccidiosis:

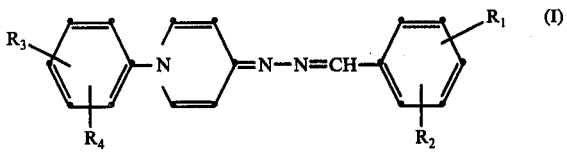

wherein $R_1$ and $R_3$ are each separately selected from halogen, haloalkyl, alkylthio and cyano wherein the alkyl group contains 1 to 3 carbon atoms; and $R_2$ and $R_4$ are each separately selected from hydrogen and halogen.

As used in this specification, the prefix "lower" is meant to include groups having from 1 to 3 carbon atoms, i.e., methyl, ethyl and propyl including the isomers of propyl. Also, in this specification the term, "halo" is intended to include fluoro, chloro, bromo and iodo.

Although the substituents $R_1$ and $R_3$ may be positioned anywhere on the phenyl rings, a preferred group of 1-substitutedphenyl-4(1H)-pyridinone hydrazones are those wherein $R_1$ and $R_3$ are at the para positions having the structural formula (II) and the non-toxic, pharmacologically acceptable salts thereof:

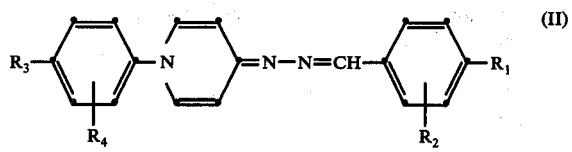

wherein $R_1$, $R_2$, $R_3$ and $R_4$ are as defined above in formula (I).

A more preferred group of 1-substitutedphenyl-4(1H)-pyridinone hydrazones are those of formula (III) below and the non-toxic, pharmacologically acceptable salts thereof wherein the substitutedphenyl attached to the 1-position of the pyridinone ring is a para-monosubstitutedphenyl group:

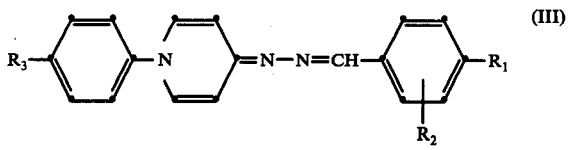

wherein $R_1$ and $R_3$ are each separately selected from halogen, haloalkyl, alkylthio and cyano wherein the alkyl group contains 1 to 3 carbon atoms; and $R_2$ is hydrogen or halogen.

A still more preferred group of 1-substitutedphenyl-4(1H)-pyridinone hydrazones are those corresponding to formula (III) where $R_3$ is halogen and the corresponding non-toxic, pharmacologically acceptable salts thereof. Chlorine is the preferred halogen.

The most preferred group of 1-substituted-4-(1H)-pyridinone hydrazones are those having the structural formula (IV) and the corresponding non-toxic, pharmacologically acceptable salts thereof:

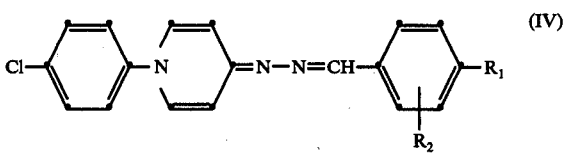

wherein $R_1$ is fluorine, chlorine, bromine, trifluoromethyl, methylthio or cyano; and $R_2$ is hydrogen, chlorine or bromine.

A preferred group of compounds of the present invention are those designated:
1-[(4-chlorophenyl)-4(1H)-pyridinone]-2-[(4-bromophenyl)methylene]hydrazone; 1-[(4-chlorophenyl)-4(1H)-pyridinone]-2-[(3,4-dichlorophenyl)methylene]-hydrazone; and 1-[(4-chlorophenyl)-4(1H)-pyridinone]-2-[(4-chlorophenyl)methylene]-hydrazone and the non-toxic, pharmacologically acceptable salts thereof.

Included in the present invention are the non-toxic pharmacologically acceptable salts of the compounds of the present invention. In addition to the fluorosulfonate and methosulfate salts, the preferred salts are the non-toxic, pharmacologically acceptable acid addition salts of the strong mineral acids such as the hydrochloride, hydrobromide, sulfate, nitrate and monophosphate. The salts of the organic salts such as tartrate, oxalate and p-toluenesulfonate may also be used. Those salts generally considered as non-toxic are preferred when the compounds of the present invention are used an anticoccidial agents for poultry.

The desired salts are prepared from the free base (I) by treatment with the corresponding acid by conventional methods.

As described more fully below, these anticoccidial compounds are prepared by the process set forth in Scheme I:

Scheme I wherein the groups $R_3$ and $R_4$ are as defined above.

As heretofore stated, it has now been found that the 1-substitutedphenyl-4(1H)-pyridinone hydrazones of this invention are highly active against protozoa responsible for coccidiosis, and hence are particularly useful in treating and preventing coccidiosis when administered to poultry. The active compounds are conveniently fed to poultry as a component of the feed of the animals although it may also be given dissolved or suspended in the drinking water. Although the compounds of this invention are effective against the many species of Eimeria, they are especially effective against *E. tenella*.

According to a preferred aspect of this invention,

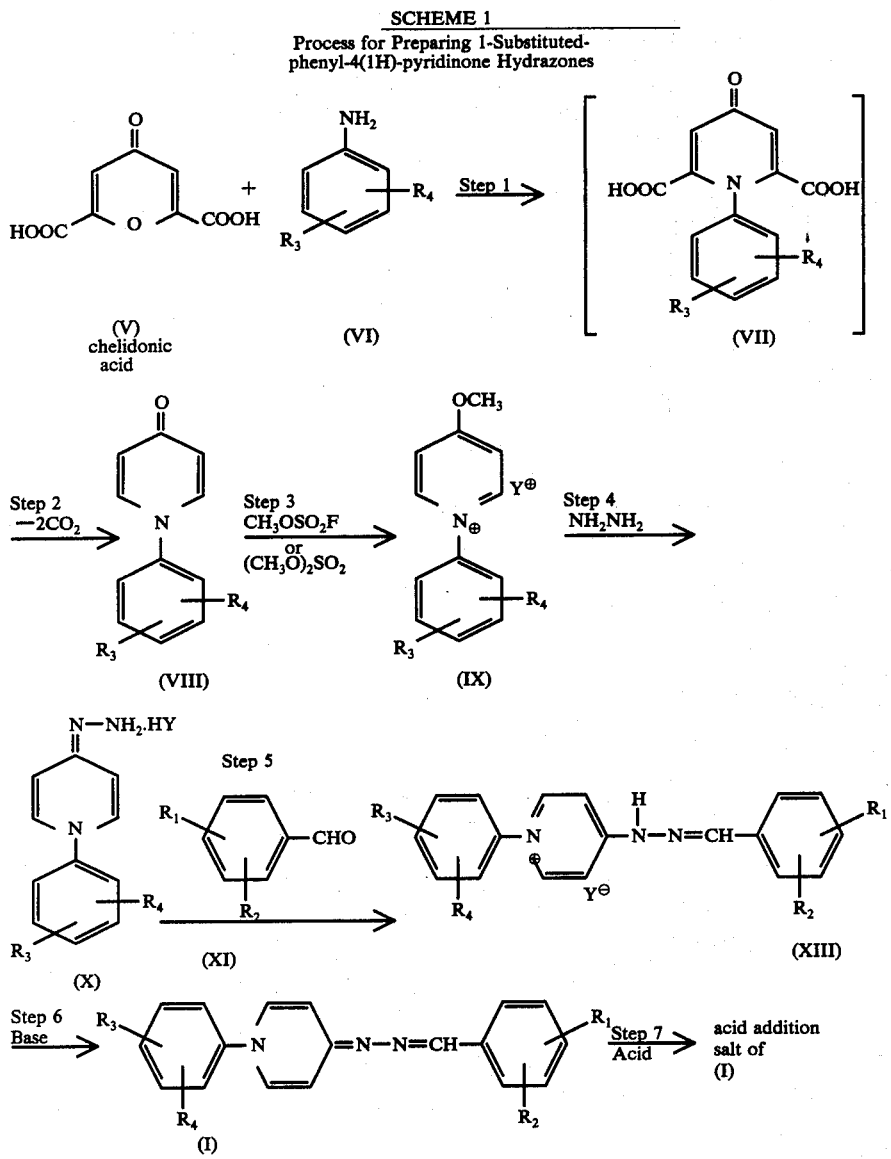

wherein $R_1$ and $R_3$ are each separately selected from halogen, haloalkyl, alkylthio and cyano wherein the alkyl group contains 1 to 3 carbon atoms; $R_2$ and $R_4$ are each separately selected from hydrogen and halogen; and Y is $SO_3F$ or $CH_3OSO_3$.

Included within the scope of the present invention are the novel intermediates (VIII), and the fluorosulfonate and methosulfate salts of (IX) and (X) set forth in novel compositions for the treatment of coccidiosis are provided which comprises one or more 1-substituted-phenyl-4(1H)-pyridinone hydrazones intimately dispersed in or intimately admixed with an inert edible carrier or diluent. By an inert edible carrier or diluent is meant one that is nonreactive with respect to the 1-substitutedphenyl-4(1H)-pyridinone hydrazones, and that may be administered with safety to the animals to be treated. The carrier or diluent is preferably one that is or may be an ingredient of the animal feed.

The compositions which are a preferred feature of this invention are the so-called feed pre-mixes in which the 1-substitutedphenyl-4(1H)-pyridinone hydrazones of this invention are present in relatively large amounts and which are suitable for addition to the poultry feed either directly or after an intermediate dilution or blending step. Examples of carriers or diluents suitable for such compositions are animal feed ingredients including edible vegetable substances such as distillers' dried grains, corn meal, citrus meal, fermentation residues, wheat shorts, molasses solubles, corn germ meal, corn cob meal, toasted dehulled soya flour, soybean mill feed, antibiotic mycelia, soya grits, and mineral substances such as ground oyster shells, Attapulgus clay, crushed dolomite and limestone. The 1-substitutedphenyl-4(1H)-pyridinone hydrazones are intimately dispersed or admixed throughout the solid inert carrier by methods such as grinding, stirring, milling, or tumbling. By selecting proper diluents and by altering the ratio of carrier to active ingredient, compositions of any desired concentration may be prepared. Formulations containing from about 1 to about 40% by weight and preferably from about 2 to about 25% by weight, of the 1-substitutedphenyl-4(1H)-pyridinone hydrazones are suitable as a pre-mix which is intended for addition to poultry feedstuffs. The active compound is usually dispersed or mixed uniformly in the diluent, but in some instances may be advantageously sorbed on the carrier. Since it is convenient for the feed manufacturer to use about one pound of feed supplement for each ton of finished feed, the preferred concentration in the supplement is usually a function of the level of active ingredient desired in the finished feed.

It is common practice to further dilute the feed pre-mix with materials such as corn meal or soybean meal before being incorporated in the animal feed. In this intermediate processing step the level of the compounds of this invention in the carrier is brought down to about 0.1 to 1.0% by weight. This dilution serves to facilitate uniform distribution of the coccidiostat in the finished feed. The finished feed is one that contains a source of fat, protein, carbohydrate, minerals, vitamins and other nutritional factors.

Very low levels of 1-substitutedphenyl-4(1H)-pyridinone hydrazones in the ultimate feed are sufficient to afford the poultry good protection against coccidiosis. Suitably the compound is administered to chickens in an amount equal to about 0.0005 to 0.10% by weight of the daily feed intake. Preferred results are obtained by feeding at a level of about 0.001 to 0.05% by weight of the finished feed, and most preferably at a level of 0.003 to 0.025% by weight. For therapeutic treatment of an established coccidial infection, higher amounts of 1-substitutedphenyl-4(1H)-pyridinone hydrazones, i.e., up to about 0.1% by weight of the feed consumed, may be employed. The most advantageous level will, of course, vary somewhat with particular circumstances such as the type and severity of the coccidial infection to be treated and the likelihood of reinfection.

It will likewise be understood by those skilled in this art that special feed supplement formulations and finished animal feeds containing vitamins, antibiotics, growth-promoting agents and other nutritional substances may include one or more compounds of this invention.

Animal feed pre-mixes having the following compositions are prepared by intimately mixing the 1-substitutedphenyl-4(1H)-pyridinone hydrazones and the particular edible solid diluent or diluents.

|   |   | lbs. |
|---|---|---|
| A. | 1-[(4-chlorophenyl)-4(1H)-pyridinone]-2-[(4-bromophenyl)methylene]hydrazone | 7.5 |
|   | Distillers' dried grains | 92.5 |
| B. | 1-[(4-chlorophenyl)-4(1H)-pyridinone]-2-[(3,4-dichlorophenyl)methylene]hydrazone | 5.0 |
|   | Soybean mill feed | 50.0 |
|   | Fine soya grits | 45.0 |
| C. | 1-[(4-chlorophenyl)-4(1H)-pyridinone]-2-[(4-chlorophenyl)methylene]hydrazone | 10.0 |
|   | Molasses solubles | 90.0 |

These supplements are made by mechanical milling or mixing of the ingredients to insure uniform distribution of the active compound.

This invention is not limited to anticoccidial compositions having the 1-substitutedphenyl-4(1H)-pyridinone hydrazones as the sole active ingredient of this invention. Compositions may be prepared containing a compound of this invention admixed with one or more other coccidiostats such as sulfaquinoxaline, other sulfa compounds, 4,4'-dinitrocarbanilide/2-hydroxy-4,6-dimethylpyrimidine complex, 3,3'-dinitrodiphenyldisulfide, 5-nitrofurfural semicarbazone, amprolium, zoalene, buqinolate, ethopabate, Coydon, Cycostat, Coban, 9-(2-chloro-6-fluorobenzyl)adenine and the like.

In the above discussion of this invention, emphasis has been placed on solid composition wherein the active ingredient is mixed with an edible carrier in a feed supplement or in the final poultry feedstuff. This is the preferred method of administering the 1-substitutedphenyl-4(1H)-pyridonone hydrazones of this invention.

An alternate method of treatment is to dissolve or suspend the 1-substitutedphenyl-4(1H)-pyridinone hydrazones in the drinking water of animals. This method can be used to advantage in flocks having an established infection, because infected birds tend to consume less feed. The quantity of coccidiostat which may be administered in this fashion is, of course, limited by the solubility of the product in water or by the quantity that may be suspended in the water without undue settling. The preferred dose levels in the drinking water are usually somewhat less than those employed in a solid feed inasmuch as poultry drink about twice as much as they eat.

The compounds of this invention are active anticoccidial agents and are employed in the above anticoccidial compositions. They are prepared by the process set forth in Scheme I.

With reference to Scheme I, Step 5 the 1-substitutedphenyl-4(1H)-pyridinone hydrazones of the present invention are prepared by the reaction of a 1-substitutedphenyl-4(1H)-pyridinone hydrazone fluorosulfonate or methosulfate, (X), of the present invention with an appropriately substituted benzaldehyde, (XI). The reaction is carried out by warming an aqueous alcohol solution of (X) and (XI). The ratio of alcohol to water is not critical provided a sufficient quantity of each is present to dissolve the reactants. A suitable ratio is approximately 50:50. The reaction may be conducted in the temperature range from 0° C. to the reflux temperature of the solvent mixture. A convenient, suitable temperature is steam bath temperature. The reaction time is from 1minute to 12 hours depending on the temperature and reactivity of the starting materials. At steam bath temperatures the reaction, in most cases, is essentially complete within 1 hour. The product is conveniently isolated by concentrating the reaction solution to remove most of the alcohol and cooling to allow crystallization of the product. The product is obtained as the fluorosulfonate or methosulfate salt (XII). The free base (I) can be obtained by treatment of the salt with aqueous alkali solution (Step 6 and said free base can be treated by conventional methods with an acid to obtain non-toxic, pharmacologically acceptable salts.

The substituted benzaldehydes (XI) can be prepared by methods known to those skilled in the art.

The 1-substitutedphenyl-1(1H)-pyridinone hydrazone fluorosulfonates or methosulfates, (X), of the present invention are prepared by reacting an alcohol suspension of the corresponding 1-substituted-4-methoxypyridinium fluorosulfonate or methosulfate, (IX), of the present invention with excess hydrazine (Step 4). The temperature of the reaction is not critical. The reaction may be conducted in the temperature range from 0° C. to the reflux temperature of the solvent. A convenient, suitable temperature is the reflux temperature of the alcohol solvent. The reaction time is from 1 minute to 24 hours depending on the temperature employed. At reflux temperature, the reaction is essentially complete within a few minutes after the starting material has dissolved. The product is isolated by allowing the reaction solution to stand at room temperature until crystallization of the product is complete.

The 1-substituted-4-methoxypyridinum fluorosulfonate or methosulfate, (IX), of the present invention is prepared by the reaction of a solution of a 1-substituted-4(1H)-pyridinone, (VIII), with a methylating agent such as methyl fluorosulfonate or dimethyl sulfate (Step 3). A suitable solvent may be selected from dyglyme, methylene chloride, tetrahydrofuran and dimethoxyethane. The preferred solvent is dimethoxyethane. The temperature of the reaction is not critical. The reaction may be conducted in the temperature range from 0° C. to the reflux temperature of the solvents. A convenient temperature is the reflux temperature of the solvent. A suitable method is to add the methyl fluorosulfonate or dimethyl sulfate to a refluxing solution of (VIII). In most cases the reaction is rapid and product begins to crystallize out of the reaction immediately. The reaction is completed by further stirring at room temperature and finally cooling at 0° C. to 10° C. to allow complete crystallization of the product, (IX).

In the case wherein dimethyl sulfate is used, the anion in compound (IX) will be the methosulfate. The process is illustrated by the following equation:

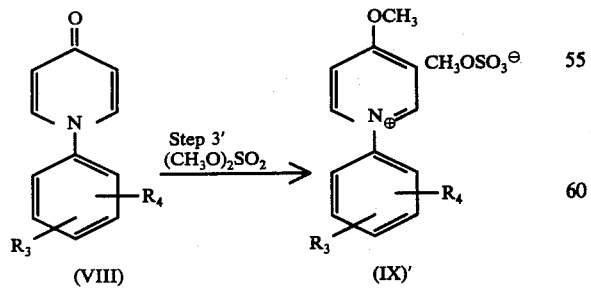

It is to be understood that compounds resulting from Steps 4 and 5 will also yield the corresponding methosulfate. The methosulfate can be converted to the free base (I) as set forth in Step 6. The free base (I) may be converted to a non-toxic, pharmacologically acceptable acid addition salt by treatment with acid by conventional methods.

The fluorosulfonate salts as well as the corresponding methosulfate of (XII) are useful as anticoccidial agents.

The necessary 1-substitutedphenyl-4(1H)-pyridinones, (VIII), are prepared by the process set forth in D. Vorlander, Ber., 58, 1908 (1925).

The following Examples are set forth to illustrate the invention and are not to be construed as limitations thereon.

EXAMPLE 1

Preparation of 1-(4-Chlorophenyl)-4-methoxypyridinium Fluorosulfonate

A solution of 18.7 g. (0.091 mole) of dried 1-(4-chlorophenyl)-4(1H)-pyridinone [prepared by the process set forth in D. Vorlander, Ber., 58, 1908 (1925)] in 160 ml. of dimethoxyethane was heated to reflux. Without further external heating, 14.2 g. (0.123 mole) of methyl fluorosulfonate was added gradually. The mixture boiled vigorously during the addition and crystalline product started to separate. After the addition was complete, the mixture was stirred at room temperature for 1 hour and then cooled to 10° C. The product was collected by filtration, washed with cold dimethoxyethane and ether and dried in vacuo: yield 28.0 g. (96.5%); m.p. 182°–185° C.; NMR (DMSO-$d_6$) $\delta$4.26 (s, 3H, $CH_3O$), 6.27 (d, 2H, $\beta$-pyridyl H), 6.32 (s, 4H, aromatics), 7.62 (d, 2H, $\alpha$-pyridyl H). The elemental analyses for C, H, N and Cl were within ±0.4% of the theoretical values.

EXAMPLE 2

Preparation of 1-(4-Chlorophenyl)-4(1H)-pyridinone Hydrazone Fluorosulfonate

To a suspension of 3.2 g. (0.01 mole) of 1-(4-chlorophenyl)-4-methoxypyridinium fluorosulfonate, prepared by the process set forth in Example 1, in 20 ml. methanol was added 0.4 g. anhydrous hydrazine. The mixture was heated to boiling for a few minutes and the resulting clear orange solution was kept overnight at room temperature. The product, in the form of orange crystals, was obtained in two crops. The total weight was 2.97 g. (93%). The product was recrystallized from methanol, m.p. 174°–176° C. The elemental analyses for C, H, N and Cl were within ±0.4% of the theoretical values.

EXAMPLE 3

Preparation of 4-Chlorobenzaldehyde 1-(4-Chlorophenyl)-4-(1H)-pyridinylidene Hydrazone Fluorosulfonate To a solution of 2.4 g. (7.5 mmole) of 1-(4-chlorophenyl)-4(1prepared H)-pyridinone hydrazone fluorosulfonate, prepared by the process set forth in Example 2, in 35 ml. ethanol and 30 ml. water was added a solution of 1.27 g. (9 mmole) of p-chlorobenzaldehyde in 5ml. ethanol. After heating the reaction mixture on the steam bath for 3 minutes, the mixture was concentrated to remove most of the ethanol, cooled and the product collected by filtration. Yield 3.1 g. (94%), recrystallized from EtOH—$H_2O$, m.p. 252°–253° C. The elemental analyses for C, H, N and Cl were within ±0.4% of the theoretical values.

EXAMPLE 4

Conversion of 4-Chlorobenzaldehyde 1-(4-Chlorophenyl)-4(1H)-pyridinylidene Hydrazone Fluorosulfonate to the Free Base A sample of 4-chlorobenzaldehyde 1(4-chlorophenyl)-4(1H)-pyridinylidene hydrazone fluorosulfonate was partitioned between methylene chloride and 2N-NaOH. The organic layer was concentrated to dryness and the residue recrystallized from ethanol-water; m.p. 165°–166° C. The elemental analyses for C, H, N and Cl were within ±0.4% of the theoretical values.

EXAMPLE 5

Preparation of 4-Chlorobenzaldehyde 1(4-Chlorophenyl)-4(1H)-pryidinylidene Hydrazone Free Base Directly To a solution of 2.4g. (7.5 mmole) of 1-(4-chlorophenyl)-4(1H)-pyridinone hydrazone fluorosulfonate in 15 ml. of 0.5N-NaOEt in ethanol at 30° C. was added 1.27 g. (9 mmole) of p-chlorobenzaldehyde. After stirring at 30° to 35° C. for 0.5 hours, the solution was refrigerated. The yield of 4-chlorobenzaldehyde 1(4-chlorophenyl)-4(1H)-pyridinylidene hydrazone free base in two crops was 2.3 g. (90%). After recrystallization from ethanol-water, m.p. 165°–166° C. The elemental analyses for C, H, N and Cl were within ±0.4% of the theoretical values.

The following additional compounds were prepared by the method set forth in Examples 3 and 4. An analogous quantity of the appropriate substituted benzaldehyde is employed in the manner of the p-chlorobenzaldehyde of Example 3. Thus, to prepare 4-bromobenzaldehyde 1(1(4-chlorophenyl)-4(1H)-pyridinylidene hydrazone fluorosulfonate there is used an equivalent amount of p-bromobenzaldehyde in place of the p-chlorobenzaldehyde in Example 3. The fluorosulfonate salt thus obtained is converted to the free base, when desired, by the process set forth in Example 4. Said free base can be converted to non-toxic, pharmacologically acceptable salts by treatment with acid using conventional methods.

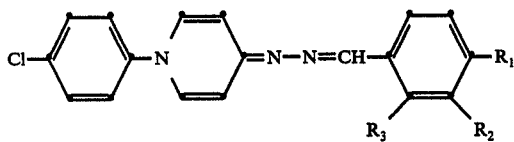

| Example No. | $R_1$ | $R_2$ | $R_3$ | % Yield | Recryst. Solvent | Melting Point ° C. |
|---|---|---|---|---|---|---|
| 6 | Br | H | H | 98% | EtOH—H$_2$O | 173–4 |
| 7 | F | H | H | 96% | EtOH—H$_2$O | 135–6 |
| 8 | CF$_3$ | H | H | 92% | EtOH—H$_2$O | 143–5 |
| 9 | CN | H | H | 97% | EtOH—H$_2$O | 192–3 |
| 10 | SCH$_3$ | H | H | 93% | EtOH | 164–5 |
| 11 | Cl | Cl | H | 80% | EtOH—H$_2$O | 177–9 |
| 12 | Cl | H | Cl | 95% | EtOH—H$_2$O | 164–5 |

What is claimed is:

1. A compound having the structure:

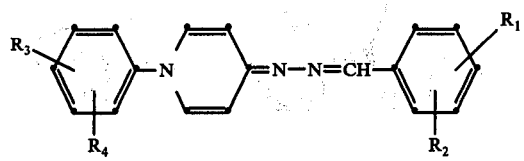

wherein $R_1$ and $R_3$ are each separately selected from halogen, haloalkyl, alkylthio and cyano wherein the alkyl group contains 1 to 3 carbon atoms; and $R_2$ and $R_4$ are each separately selected from hydrogen and halogen and the corresponding non-toxic, pharmacologically acceptable salts thereof.

2. The compound according to claim 1 having the structure:

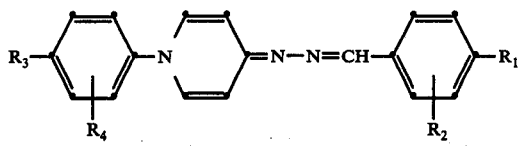

3. The compound having the structure:

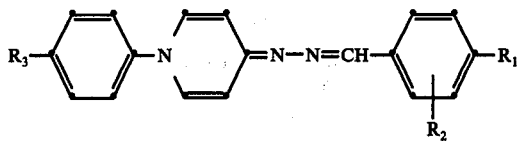

wherein $R_1$ and $R_3$ are each separately selected from halogen, haloalkyl, alkylthio and cyano wherein the alkyl group contains 1 to 3 carbon atoms; and $R_2$ is hydrogen or halogen and the corresponding non-toxic, pharmacologically acceptable salts thereof.

4. The compound according to claim 3 wherein $R_3$ is halogen.

5. The compound having the structure:

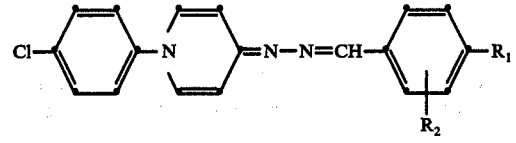

wherein $R_1$ is fluorine, chlorine, bromine, trifluoromethyl, methylthio or cyano; and $R_2$ is hydrogen, chlorine or bromine and non-toxic, pharmacologically acceptable salts thereof.

6. The compound according to claim 5 wherein $R_1$ and $R_2$ are hydrogen, chlorine or bromine with the proviso that $R_1$ and $R_2$ are not both hydrogen.

7. The compound according to claim 6 selected from the group consisting of:
1-[(4-chlorophenyl)-4(1H)-pyridinone]-2-[(4-bromophenyl)methylene]hydrazone; 1-[(4-chlorophenyl)-4(1H)-pyridinone]-2-[(3,4-dichlorophenyl)methylene]hydrazone; and 1[4-chlorophenyl)-4(1H)-pyridinone]-2-[(4-chlorophenyl)methylene]hydrazone and non-toxic, pharmacologically acceptable salts thereof.

8. The process for preparing the compound having the structure:

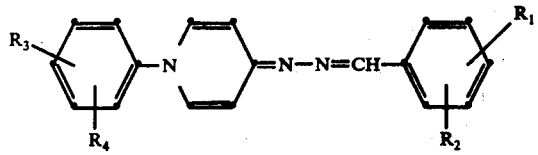

or a non-toxic, pharmacologically acceptable salt thereof wherein $R_1$ and $R_3$ are each separately selected from halogen, haloalkyl, alkylthio and cyano wherein the alkyl group contains 1 to 3 carbon atoms; and $R_2$ and $R_4$ are each separately selected from hydrogen and halogen which comprises reacting the hydrazone compound having the structure:

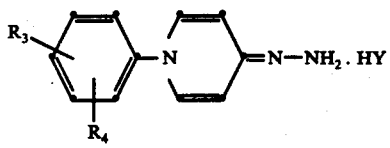

wherein $R_3$ and $R_4$ are as defined above and Y is $SO_3F$ or $CH_3OSO_3$ with the substituted benzaldehyde having the structure:

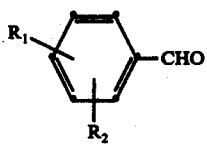

wherein $R_1$ and $R_2$ are as defined above to obtain the fluorosulfonate or methosulfate salt.

9. The process for preparing the compound having the structure:

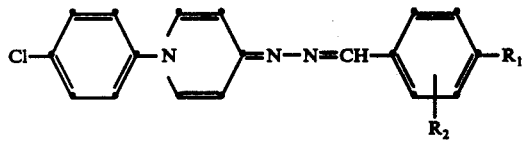

according to claim 8 comprising converting said salt to the free base and treating said free base with an acid.

10. A composition for the treatment of coccidioisis comprising an inert carrier and an effective amount of a compound having the structure:

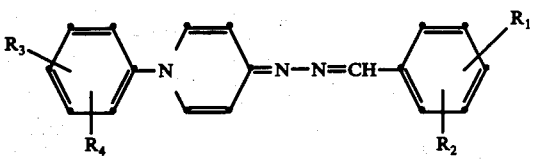

wherein $R_1$ and $R_3$ are each separately selected from halogen, haloalkyl, alkylthio and cyano wherein the alkyl group contains 1 to 3 carbon atoms; and $R_2$ and $R_4$ are each separately selected from hydrogen and halogen and the non-toxic, pharmacologically acceptable salts thereof.

11. A composition according to claim 10 wherein said compound comprises from 0.0005% to 0.1% by weight of said composition.

12. A composition according to claim 11 wherein said compound is selected from the group consisting of:
1-[(4-chlorophenyl)-4(1H)-pyridinone]-2-[(4-bromophenyl)methylene]hydrazone; 1-[(4-chlorophenyl)-4(1H)-pyridinone]-2-[(3,4-dichlorophenyl)methylene]hydrazone; and 1-[(4-chlorophenyl)-3(1H)pyridinone]-2-[(4-chlorophenyl)methylene]hydrazone and the non-toxic, pharmacologially acceptable salts thereof.

13. A composition according to claim 10 wherein said composition is a feed premix and said compound comprises from about 1 to about 40% by weight of the premix.

14. A composition according to claim 13 wherein said composition is a feed premix and said compound comprises from about 2% to about 25% by weight of the premix.

15. A composition according to claim 10 wherein said composition is a feed premix and said compound is selected from the group consisting of:
1-[(N-chlorophenyl)-4(1H)-pyridinone]-2-[(4-bromophenyl)methylene]hydrazone; 1-(4-chlorophenyl)-4(1H)-pyridinone]-2-[(3,4-dichlorophenyl)methylene]hydrazone; and 1[(4-chlorophenyl)-4(1H)-pyridinone]-2-[(4-chlorophenyl)methylene]hydrazone and the non-toxic, pharmacologically acceptable salts thereof.

* * * * *